United States Patent [19]

Forintos

[11] Patent Number: 4,686,981
[45] Date of Patent: Aug. 18, 1987

[54] SURGICAL INSTRUMENT ESPECIALLY FOR PERFORMING NEUROSURGICAL OPERATIONS

[76] Inventor: László Forintos, Amerikai ut 57, 1145 Budapest, Hungary

[21] Appl. No.: 684,333
[22] PCT Filed: Mar. 28, 1984
[86] PCT No.: PCT/HU84/00020
   § 371 Date: Nov. 26, 1984
   § 102(e) Date: Nov. 26, 1984
[87] PCT Pub. No.: WO84/03829
   PCT Pub. Date: Oct. 11, 1984

[30] Foreign Application Priority Data

Mar. 28, 1983 [HU] Hungary .............................. 1037/83

[51] Int. Cl.⁴ ............................................. A61B 17/39
[52] U.S. Cl. .................................. 128/303.17; 604/119
[58] Field of Search ...................... 128/303.11–303.17, 128/395, 303 R, 303.1; 604/118–119; 148/13

[56] References Cited

U.S. PATENT DOCUMENTS

| 3,825,004 | 7/1974 | Durden, III | 128/303.17 X |
| 3,828,780 | 8/1974 | Morrison, Jr. | 128/303.17 |
| 3,974,833 | 8/1976 | Durden, III | 128/303.17 X |
| 4,207,874 | 6/1980 | Choy | 128/303.1 X |
| 4,307,720 | 12/1981 | Weber, Jr. | 128/303.17 X |
| 4,369,785 | 1/1983 | Rehkopf et al. | 604/119 |
| 4,463,759 | 8/1984 | Garito et al. | 128/303.17 X |
| 4,512,343 | 4/1985 | Falk et al. | 128/303.17 |

FOREIGN PATENT DOCUMENTS

| 2235669 | 3/1975 | France | 128/303.17 |
| 2060397 | 5/1981 | United Kingdom | 128/303.1 |

*Primary Examiner*—Kyle L. Howell
*Assistant Examiner*—Angela D. Sykes
*Attorney, Agent, or Firm*—Karl F. Ross; Herbert Dubno

[57] ABSTRACT

The invention relates to a surgical instrument especially for performing neurosurgical operations, having a flexible suction tube to be connected to a vacuum source, the suction tube being provided with a finger plate having a hole communicating with the inner space of the suction tube. The suction tube is provided with an electric connector which can be connected to a high-frequency power source and the portion of said suction tube reaching the locality of the operative field—with the exception of the tube end functioning as a coagulating end—being provided on its outer surface with an electrically insulating, flexible plastic coating.

The basic point of the invention is that the suction tube (2) is formed by a silver pipe with a coat (4) made of a synthetic thermoplastic material of the polyamide type.

10 Claims, 4 Drawing Figures

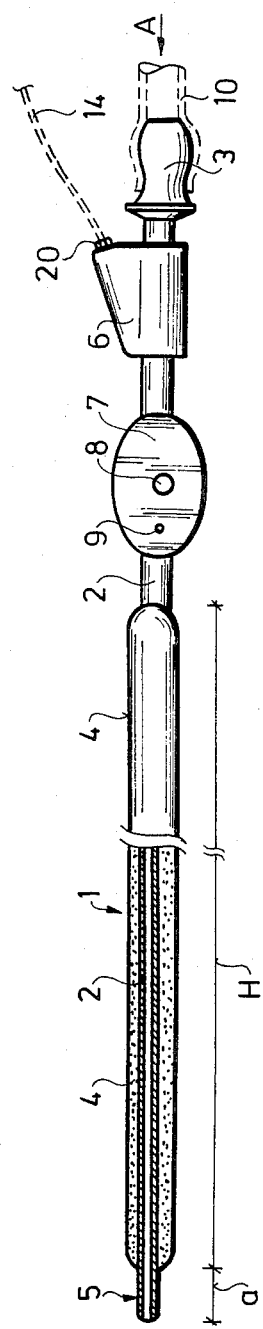
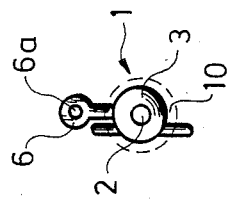

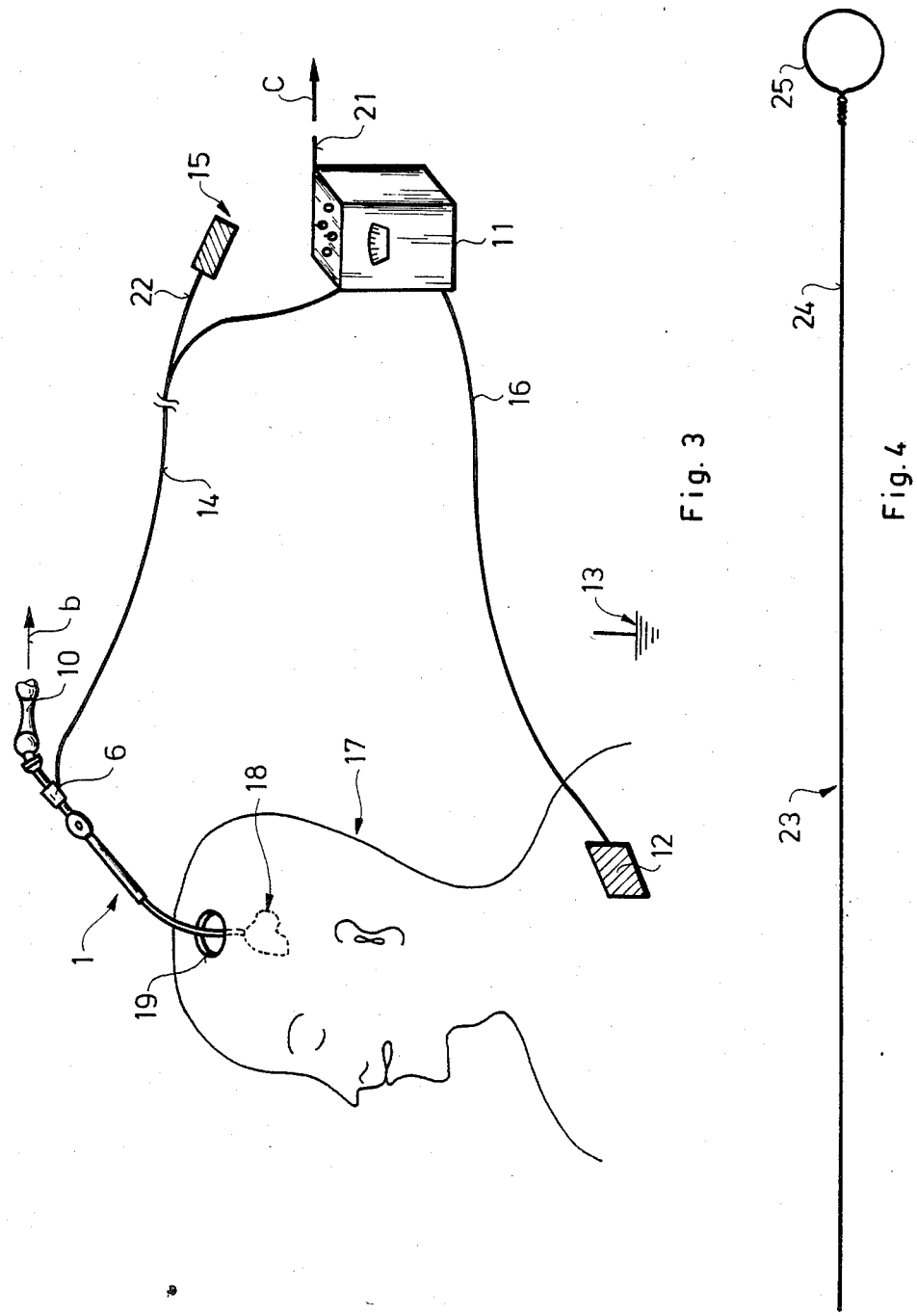

SURGICAL INSTRUMENT ESPECIALLY FOR PERFORMING NEUROSURGICAL OPERATIONS

CROSS-REFERENCE TO RELATED APPLICATIONS

This application is a National Phase Application corresponding to PCT/HU 84/00020 filed Mar. 28, 1984 and based, in turn, upon Hungarian application No. 1037/83 filed Mar. 28, 1983.

FIELD OF THE INVENTION

The invention relates to a surgical instrument which can advantageously be used especially for performing neurosurgical operations.

BACKGROUND OF THE INVENTION

When performing neurosurgical operations, e.g. in cerebral surgery, there is a grave problem with respect to removal of blood, secretions, etc. from the operative field, usually by suction, and to stop bleeding of the blood-vessels, to close the arteries referred to as coagulation, because the operative field is difficult and elaborate to reach, and because several kinds of surgical instruments have to be used alternately. Some of the instruments are connected to a high frequency power source; therefore the instruments must be electrically insulated in order to prevent "arcing" which may occur when two different instruments are present simultaneously, e.g. in the skull. Such instruments include the so-called bipolar forceps used to stop bleeding of the blood-vessels (coagulation). This important group of instruments comprises about 40 to 50 units of different forms, and it depends on the organ to be operated and on the nature of the operation which kind of instrument is used. When using the bipolar forceps, the electric circuit is closed and the end of the blood-vessel being pinched between the forceps is so to say "welded" by the high frequency current. Before introduction of the bipolar forceps, the suction probe has to be removed. It is disadvantageous that separate persons are needed to handle the suction instrument and the bipolar forceps. These latter have also the disadvantage that due to mechanical overstrain and to the everyday gas sterilization, they deteriorate, are damaged quickly and require time for replacement of the unusable forceps.

Suction instruments, as used today, are constructed as thin, rigid pipes made of a special metal or metal alloy, connected to the vacuum source of the operating room and operated by temporary opening and closing the vacuum—as needed. Their up-to-date types are available—at very high prices—in the form of sets comprising several pipes bent at different—predetermined—angles. They are able to perform only one funtion i.e. suctioning. A whole series of suction tubes with different bending angles are needed, as the more flexibly the suction tube or the series of suction tubes reach that area where the fluids super-fluous blood etc. have to be sucked from, the more reduced the operative field may be. The cost factors are even less favourable in the case of disposable suction tubes destined for a single application, while their value in use is not or at least not substantially better.

OBJECT OF THE INVENTION

The object of the invention is to provide a surgical instrument especially for performing neurosurgical operations, which can be used both for the function of suctioning and coagulating, can be bent at any optional angles, is electrically insulated and resists mechanical stresses as well as gas sterilization.

SUMMARY OF THE INVENTION

The invention is based upon the recognition that when the suction tube is made of a material which is easy to bend, significantly resists flexing, is corrosion-proof, is conductive and non-toxic, and is coated with a plastic material resisting flexing and gas sterilization over that area which contacts the operative field, except near its tip, and when this suction tube is equipped with an electric connector with the aid of which it can be connected to a high frequency power source, then both coagulating and sucking may be performed by one instrument of maximum flexibility.

The surgical instrument of the invention has a suction tube which can be connected to a vacuum source, the suction tube being provided with a finger plate having a hole communicating with the inner space thereof. The suction tube is formed as a flexible silver pipe, the portion of said suction tube in the operative field—with the exception of the pipe end functioning as a coagulating end—being provided on its outer surface with an electrically insulating, flexible plastic coating, and an electric connector enabling connection of the suction tube to the high frequency power source. Expediently, the suction tube has a plastic coating made of a synthetic thermoplastic material of the polyamide type, being advantageously a plastic coating made of polyamide-11 produced by condensation of 11-amino-undecane carboxylic acid of the formula $H[HN-(CH_2)_{10}-CO]nOH$ based on castor oil.

According to a further feature of the invention, the electric connector is arranged between the finger plate and a connecting piece provided on the end of the suction tube being opposite to the coagulating end, and in a cable joined to the electric connector, there is inserted a pedal enabling switching on and off the electric circuit. According to a further embodiment of the invention, the end portion of the suction tube functioning as a coagulating end, has a lesser thickness and/or a smaller diameter than the other part of the tube. The plastic coating is present on the portion between the coagulating end and the finger plate and its length is several times, advantageously about 10 to 20 times, longer than the length of the naked pipe end serving as the coagulating end. In order to enable a fine adjustment of the sucking effect, there may be formed in the finger plate two holes of different diameters communicating with the inner space of the tube.

Finally, it is advantageous when the electric connector and the electric cable joined thereto are connected together in a manner enabling their rotation in relation to each other, and when the instrument is equipped with a cleaning means consisting of a metal, e.g. a steel, filament having an outer diameter smaller than the inner diameter of the suction tube and of a handle arranged at the end thereof.

BRIEF DESCRIPTION OF THE DRAWING

The invention will be described below with reference to the accompanying drawing which shows an advantageous embodiment of the instrument as well as a possible mode of its use. In the drawing FIG. 1 shows the instrument in a longitudinal axial section, partly in side elevation;

FIG. 2 is a view taken in the direction of arrow A of FIG. 1;

FIG. 3 shows the instrument according to FIGS. 1 and 2 in perspective view in use, during performing an operation and shows diagrammatically the auxiliary devices needed to operate the instrument; and FIG. 4 shows in elevation a means for cleaning the instrument according to FIG. 1.

SPECIFIC DESCRIPTION

The surgical instrument as shown in FIGS. 1 and 2, having as a whole the reference numeral 1, comprises a suction tube 2 made of silver, having a diameter of 0.5 to 1 mm and a length of about 20 cm. At one end of the suction tube 2 there is arranged a connecting piece 3 by the aid of which a hose 10 shown in broken lines in FIGS. 1 and 2 can be connected to the suction tube 2; the function of the hose 10 will be described later.

The end 5 of the suction tube 2 opposite the connecting piece 3 serves for performing coagulation. The coagulating end 5 of a length a C the value of a may be a few millimeters, preferably not greater than 1 cm. is bare, i.e. is formed by the silver pipe itself, while a portion H rearwardly of the coagulating end 5 having a length of about 10 to 20 cm is provided with a plastic coating 4. It is understood that the numeral data are only of informative character, the instrument may be constructed also of different dimensions.

The silver pipe manufactured from industrial silver by drawing, has excellent properties for performing the operations aimed at with the instrument, it can be made flexible by heat treatment, resists even frequent flexing, has a favorable electric conductivity, can be sterilized, is non-toxic, is fully corrosion-proof and, finally, plastics can excellently adhere thereto.

Also the plastic coating 4 is non-toxic, sterilizable and resists gas sterilization. It must, like the silver pipe, be flexible and resist frequent flexing, i.e. mechanical stresses. Further, it must be an electrically insulating material. All these requirements are met by synthetic thermoplastic materials of the polyamide type. The raw material used for the manufacture is castor oil comprising mainly glycerides of ricinoleic acid. The castor oil is converted with methanol into ricinoleic acid ester. Under the effect of heat treatment, the esters of the ricinoleic acid will be decomposed to enanthol and undecylenic acid methyl ester, this latter being hydrolyzable to undecylenic acid which is converted by amination into 11-amino-undecane carboxylic acid. From this polyamide-11 is formed by polycondensation, having the following formula:

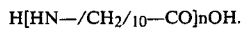

This product is marketed in the form of granules or powder under the name RILSAN. The powdered product is then applied—by hot melting techniques—onto the outer surface of the section tube 2 of heat treated silver, over the portion of a length H as mentioned above (FIG. 1), forming thereby a minimum thickness (on the order of a few tenths of a millimeter) plastic coating 4.

As shown in FIG. 1, proceeding from the coagulation end 5 towards the connecting piece 3, there are connected to the suction pipe 2 first a finger plate 7 and then an electric connector 6. The finger plate 7 can be fixed, e.g. by welding or by soldering, to the suction tube 2, is oviform and its size corresponds to that of the thumb. In the finger plate 7 there are formed a large hole 8 and a small hole 9, both communicating with the inner space of the suction tube 2, and suction may be controlled, started, stopped and interrupted by either covering the hole or holes or allowing them to open freely.

Between the finger plate 7 and the connecting piece 3 there is fixed to the suction tube 2 the electric connector 6 made expediently also of industrial silver, through which an electric connection may be established between the suction tube 2 and the high frequency power source, by inserting a plug 20 attached to an electric cable 14 into the socket 6a (FIG. 3). In FIG. 1 the cable 14 is shown in broken lines. Conveniently, the plug 20 is an interchangeable piece ensuring that all electric instruments used in the operating room can be powered via the cable 14. Besides, the plug and the connector are connected together by a rotatable joint so that, the operating surgeon may use the instrument by turning it in any direction.

In FIG. 3 there is shown the mode of use of the surgical instrument 1 according to the invention. The hose 10 usually a rubber hose) adjoining the connecting piece 3 (FIG. 1) leads as shown by arrow b to a vacuum source (not shown). The electric cable 14 connected to the electric connector 6 runs to the high frequency apparatus 11 which is also connected by means of an electric cable 21 to a 220 V power source, e.g. to the electric network, as shown by arrow c. It is to be noted that the high frequency apparatus is shown per se and may be e.g. of the type ERBOTOM. As is also well known, in hospitals there is usually available a central vacuum source since it is needed also for other purposes. To a branch 22 of the electric cable 14 there is connected a pedal 15. By operating this pedal 15, the instrument 1 may optionally be connected either to the vacuum to perform suction, or to the high frequency power source to perform coagulation (i.e. stopping of the blood vessels. The high frequency apparatus 11 (power source) is also joined to an electric cable 16 at the end of which there is arranged a body electrode 12 to be fixed during operation onto the body surface of the patient 17. The operating table 13 is shown only symbolically; it is connected to ground.

The instrument 1 according to the invention is used during an operation of, e.g. a brain-tumor, as follows:

In the skull of the patient 17 there is prepared—in a mannner known per se—a hole 19 by cutting out a piece of the skull and the tumor 18 marked with dotted lines in FIG. 3 is exposed, then removed. During operation, by means of the instrument 1 the blood, secretions, etc. may be sucked from the operative field and the intersected blood vessels can be coagulated. The respective actions may be performed consecutively by means of a single instrument without the need to remove it from the operative field. In order to perform alternately both actions, the operating surgeon has only to depress the pedal 15 and during sucking action, the control of suction and regulation of the sucking intensity may optionally be performed by temporary closing and opening the holes 8, 9 with the thumb. The small hole 9 is provided in order to enable a more fine control of the sucking effect, it is used first of all in special operations (e.g. in the case of aneurism). The access to the operative field—in the present case to the area round the tumor—is ensured by the instrument 1 since the suction tube 2 together with the coating 4 may optionally be bent even during the operation, thus, every point of the operative field may perfectly be reached during the whole process of the operation, in order to perform either suction or coagulation.

The cleaning means 23 shown in FIG. 4 is an essential accessory of the instrument according to the invention. It consists of a filament 24 of spring steel (stylet) and of a handle 25 formed on one end thereof. By drawing the filament 24 through the tube 2, the instrument 1 can be cleaned both during operation or thereafter. The length of the filament 24 preferably exceeds the entire length of the tube 2.

The advantageous effects attached to the invention are as follows:

This single instrument in itself is able to perform two functions which until now could be performed not only by two separate instruments but actually by to separate sets of instruments. A set of the known rigid suction tubes comprises, e.g. ten to twenty pipes, bent at different angles in order that different points of the operative field may be reached therewith. By contrast the instrument according to the invention may be bent at any optional angles—even during operation—thus, it may be adapted much more flexibly to the function to be performed than a whole set of rigid suction tubes comprising any number of pipes. Also the bipolar forceps used till now for coagulation are marketed in form of sets and it is obvious that the operating surgeon can better reach the blood vessels to be stopped at any point of the operative field by using the instrument according to the invention which may optionally be bent in any directions, than by using the known bipolar forceps. Handling this latter is more complicated than the use of the instrument according to the invention, because the blood vessel to be coagulated has to be squeezed by the forceps while my instrument need only to be touched to the blood vessel to be stopped; thus, when using the instrument according to the invention, coagulation takes place only on that desired small area where it is needed—this is due also to the insulating plastic coating—and meanwhile the instrument needs not to be kept away from the surroundings of the operative field being otherwise very limited. Besides, sucking and coagulating operations may be performed subsequently, alternately or, in principle, even simultaneously by means of the instrument according to the invention, and the instrument need—as mentioned already—not be removed from the operative field even when also other instruments are applied there, because the plastic coating guarantees an electric insulation; thus electric arcing may not occur between the different instruments. Both the silver and the polyamide-type plastic can be readily sterilized, easily flexed and resist well mechanical stresses, easily accommodating frequent flexing in alternate directions. Both the silver and the plastic material are non-toxic. The plastic coating may be manufactured in various colors which may involve practical advantages. Due to the advantageous properties of the instrument as set forth above, one hand of the surgion is free during operation. The rotating connection between the cable and the instrument enables the surgeon to perform various operations very easily, the instrument accommodating to the palm of the hand does not impede the fine motions and, a main activity of the staff, namely to ensure connection between the cable and the instrument—often associated with contact failures—may be omitted, so that the staff can better assist in the surgical part of the operation. Due to the flexible tube being able to bend in any directions, only a minimum area has to be opened as operative field. Yet, the visibility and accessability to the operative field is better, the operation may be performed faster and due to the significantly limited operative time, the patient has a better possibility of survival—e.g. in case of brain operations or other severe neuromuscular operations. Transfusion is needed to a reduced extent and due to the limited operative time, the utilization of the operating room can be improved. The instrument may be manufactured in several e.g. 8 to 10 sizes [different lengths and/or thicknesses and/or outer or inner diameters, etc.], according to the requirements as raised by different operations. The instrument is extraordinarily suitable for brain and spinal operations to be performed within deep, narrow holes and also for other operations being practically insolvable with the instruments as used today. Finally, the manufacturing costs of the instrument according to the invention are lower than that of the conventional instruments.

The invention is of course not restricted to the embodiment described above in details, but it may be realized in many other ways within the scope of the claims.

I claim:

1. In a surgical instrument for performing neurosurgical operations, having a flexible suction tube connectable to a vacuum source, the suction tube being provided with a finger plate having a hole communicating with an inner space of the suction tube, the suction tube further being provided with an electric connector connectable to a high-frequency power source, and an end which localizes a field energized by said source, a portion of said suction tube reaching the locality of said field, the tube end functioning as a coagulating end, the suction tube with the tube end being provided on its outer surface with an electrically insulating, flexible plastic coating, said tube end being exposed, the improvement wherein the suction tube is formed by a flexible silver pipe which has been heat treated to permit bending during a surgical procedure by the surgeon, and said coating is made of a polyamide synthetic thermoplastic polyamide-11 material hot-melt bonded to the heat treated flexible silver pipe and produced by condensation of 11-amino-undecane carboxylic acid to a thermoplastic of the formula

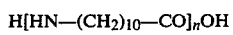

$$H[HN-(CH_2)_{10}-CO]_nOH$$

based on castor oil.

2. The improvement defined in claim 1 wherein the electric connector is arranged between the finger plate and a connecting piece provided on the end of the suction tube opposite to the coagulating end.

3. The improvement defined in claim 1 wherein a cable is joined to the electric connector, and a pedal is provided in said cable enabling an electric circuit with said power source to be switched on and off and controlling suction to the tube.

4. The improvement defined in claim 1 wherein the end of the suction tube functioning as a coagulating end, has a lesser diameter than the remainder of the tube.

5. The improvement defined in claim 1 wherein the coating is present on the portion of said tube between the coagulating end and the finger-plate and its length is at least several times longer than the length of the exposed coagulating end.

6. The improvement defined in claim 5 wherein the length of the coating is 10 to 20 times longer than the length of the exposed coagulating end.

7. The improvement defined in claim 1 wherein the finger plate is formed with two holes of different diameters communicating with the inner space of the tube.

8. The improvement defined in claim 1, further comprising a cleaning means for insertion into the suction tube including a metal filament having an outer diameter smaller than the inner diameter of the suction tube, and a handle at an end thereof.

9. The improvement defined in claim 8 wherein said metal filament is composed of steel.

10. The improvement defined in claim 1 wherein the electric connector has an electric cable joined thereto, the connector and cable being connected to enable relative rotation.

* * * * *